US00PP32434P3

(12) United States Plant Patent
Vinson

(10) Patent No.: US PP32,434 P3
(45) Date of Patent: Nov. 10, 2020

(54) ***FRAGARIA* PLANT NAMED 'JFK44'**

(50) Latin Name: ***Fragaria* x *ananassa***
Varietal Denomination: JFK44

(71) Applicant: Edward Vinson Ltd., Faversham (GB)

(72) Inventor: Peter Edward Vinson, Faversham (GB)

(73) Assignee: EDWARD VINSON LTD., Faversham (GB)

( * ) Notice: Subject to any disclaimer, the term of this patent is extended or adjusted under 35 U.S.C. 154(b) by 0 days.

(21) Appl. No.: 16/602,780

(22) Filed: Dec. 6, 2019

(65) Prior Publication Data

US 2020/0221620 P1 Jul. 9, 2020

(30) Foreign Application Priority Data

Jan. 8, 2019 (QZ) ..... PBR 20190096

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./156, 208
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new and distinct June bearing cultivar of *Fragaria* plant named 'JFK44' that is characterized by its s semi-upright growth habit, its conical shaped berries that are uniformly very large in size, its well-presented fruit on long, thick trusses, its fruits that are highly glossy and deep red in color with color retained throughout production, its vigorous growth habit with substantial fruit yields of marketable quality, and its fruit that is are produced in early-mid season.

2 Drawing Sheets

Botanical classification: *Fragaria* x *ananassa*.
Variety denomination: 'JFK44'.

CROSS REFERENCE TO A RELATED APPLICATION

This application claims priority to European Community Plant Variety Office (CPVO) Plant Breeder's Rights Application No. 2019/0096 filed on Jan. 8, 2019, under 35 U.S.C. 119(f), the entire contents of which is incorporated by reference herein.

BACKGROUND OF THE INVENTION

The present invention relates to a new and distinct cultivar of *Fragaria*, botanically known as *Fragaria* x *ananassa* 'JFK44', and will be referred to hereafter by its cultivar name, 'JFK44'. 'JFK44' is a June Bearing strawberry plant primarily adapted to the climate and growing conditions of the United Kingdom and other regions of similar climate and day length.

The new cultivar was derived from an ongoing breeding program conducted by the Inventor at a farm in Faversham, Kent, United Kingdom. The objective of the breeding program was to develop a new cultivar of *Fragaria* with high fruit yields, consistent cropping, and large, uniform fruit with firm skins, low acid content, and good eating quality. 'JFK44' arose from a controlled cross made by the Inventor in 2013 between an unnamed selection from the Inventor's breeding program, designated as accession number "JKH123" (not patented) as the female parent and an unnamed selection from the Inventor's breeding program, designated as accession number "JVB88" (not patented) as the male parent. 'JFK44' was selected as a single unique plant in the spring of 2014 from amongst the seedlings that resulted from the above cross.

Asexual reproduction of the new cultivar was first accomplished by rooting of stolons by the Inventor in Faversham, Kent, United Kingdom in 2014. Asexual propagation by rooting of stolons and tissue culture using meristematic tissue has shown that the unique characteristics of the new cultivar are stable and reproduced true to type in successive generations.

BRIEF SUMMARY OF THE INVENTION

The following traits have been repeatedly observed and represent the characteristics of the new cultivar. These attributes in combination distinguish 'JFK44' as a new and unique cultivar of *Fragaria*.

1. 'JFK44' exhibits a semi-upright growth habit.
2. 'JFK44' exhibits conical shaped berries that are uniformly very large in size.
3. 'JFK44' exhibits very well-presented fruit on long, thick trusses.
4. 'JFK44' exhibits fruits that are highly glossy and deep red in color with color retained throughout production.
5. 'JFK44' exhibits vigorous growth habit with substantial fruit yields of marketable quality.
6. 'JFK44' exhibits fruit that is are produced in early-mid season.

'JKH123', the female parent of 'JFK44', differs from 'JFK44' in having fruits that are paler in color, smaller in size and held on shorter fruit trusses, and in having lower total fruit yields. 'JVB88', the male parent of 'JFK44', differs from 'JFK44' in having fruits that are smaller with softer skin firmness, and in having lower total fruit yields.

'JFK44' can be most closely compared to the cultivars 'Flair' (U.S. Plant Pat. No. 23,162) and 'Sonata' (U.S. Plant Pat. No. 18,000).

The average fruit size of 'JFK44' is consistently much larger than that of 'Flair'. Fruit shape is similar in both varieties being predominantly conical, but evenness of shape is greater in 'JFK44' with berries of 'Flair' sometimes appearing more rounded cordate. Skin firmness is also similar in both varieties with 'JFK44' being slightly firmer than 'Flair'.

Both 'Flair' and 'JFK44' can be described as vigorous and semi-upright in their habit when grown in the United Kingdom but 'JFK44' is on average taller and has a greater average petiole length than 'Flair'. Additionally, the petiole color is darker for 'JFK44' than 'Flair'.

While average leaf color is similar between the two varieties, the leaf base of 'Flair' can be described as obtuse whereas the leaf base of 'JFK44' appears more acute in shape, making 'JFK44' leaves more elongated in shape compared to 'Flair'. However, the apex shape for both 'Flair' and 'JFK44' is similarly rounded. Leaf serrations are a sharper serrate in 'Flair' whereas 'JFK44' serrations appear more serrate to crenate in appearance. The shape of leaves in cross section for both varieties is predominantly concave and although blistering is present on both 'Flair' and 'JFK44', it is more apparent in 'JFK44'.

The flower truss position is generally level relative to the foliage for both 'JFK44' and 'Flair' even though the actual truss size differs between the two varieties. Both the peduncle and the pedicel are significantly longer in 'JFK44' compared to 'Flair' and while the diameter of the truss is greater in 'JFK44', support is still needed to support the massive 'JFK44' fruit weight. These longer trusses of 'JFK44' result in the fruit being very well displayed. The calyx of both varieties is predominantly exhibited as upwards recurved.

For 'JFK44' and 'Flair', the flower and petal sizes are similar between the two varieties. The petals usually do not overlap on fully mature flowers for both 'Flair' and 'JFK44' and both express a very similar white coloration on the petals. Both varieties have similarly upward recurving calyxes although the diameter of the calyx is greater for 'JFK44'.

'JFK44' berries are usually glossier in appearance when compared to 'Flair' and although both fruits can display a white band around the neck of the berry, it is more pronounced and common in 'Flair'. Even though both varieties have low to absent fruit surface unevenness, it appears that 'JFK44' produces on average a higher percentage of uniform fruit. The cropping season of 'Flair' is generally earlier than that of 'JFK44'.

High fruit color uniformity is present in both 'JFK44' and 'Flair' but the fruit of 'JFK44' is generally has skin color. The skin flesh color is also a deeper, darker red for 'JFK44'. The achenes present themselves differently on the surface of the fruit for each variety too. The achenes of 'Flair' are mainly sunken below the surface whereas for 'JFK44' the achenes are mostly level with the surface of the berry. Fruits for both varieties have low acid levels and a moderate sugar content.

'Sonata' is similar to 'JFK44' in having an upright growth habit and a similar calyx diameter relative to fruit diameter. 'Sonata' differs from 'JFK44' in having smaller flowers, a smaller plant height, and fruit that are smaller in size with a lighter skin color.

BRIEF DESCRIPTION OF THE DRAWINGS

The accompanying colored photographs illustrate the overall appearance and distinct characteristics of the new cultivar. The photographs were taken of 'JFK44' plants as grown in trays under polythene tunnels in substrate in Faversham, Kent, United Kingdom. The photographs were taken 3 months after planting in January from tips taken in June the year before and grown in a container until December and overwintered at −2° C.

The photograph in FIG. 1 provides a side view of 'JFK44' with fruit.

Figure 1:
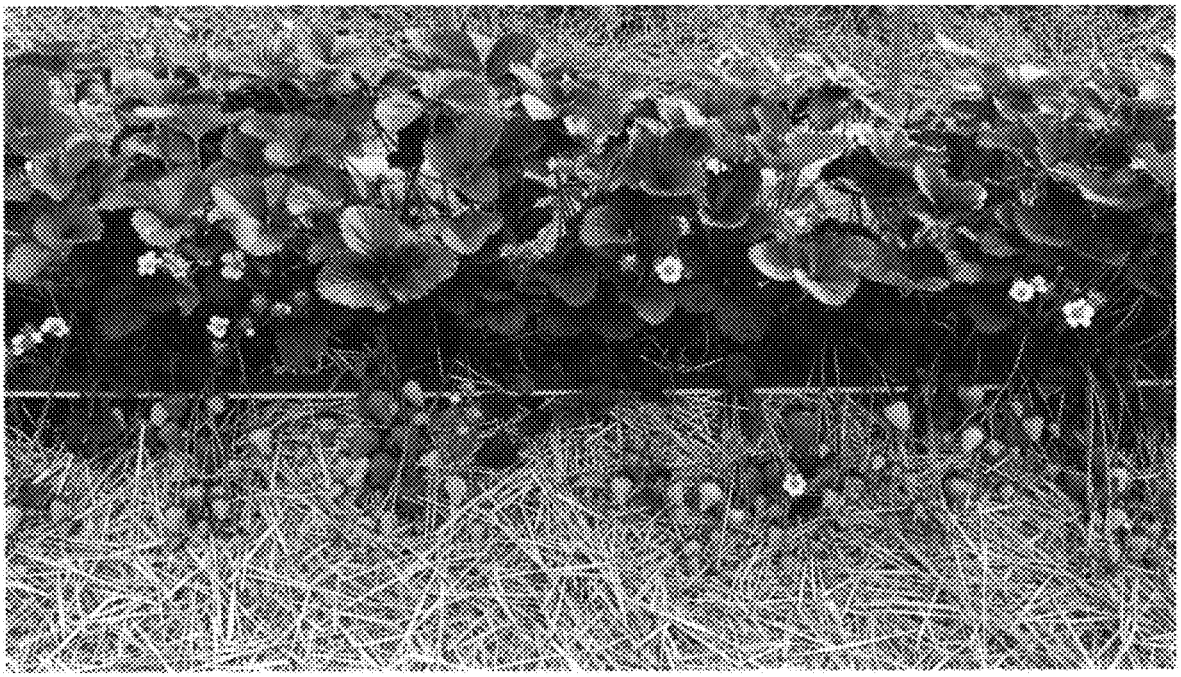
Figure 2:
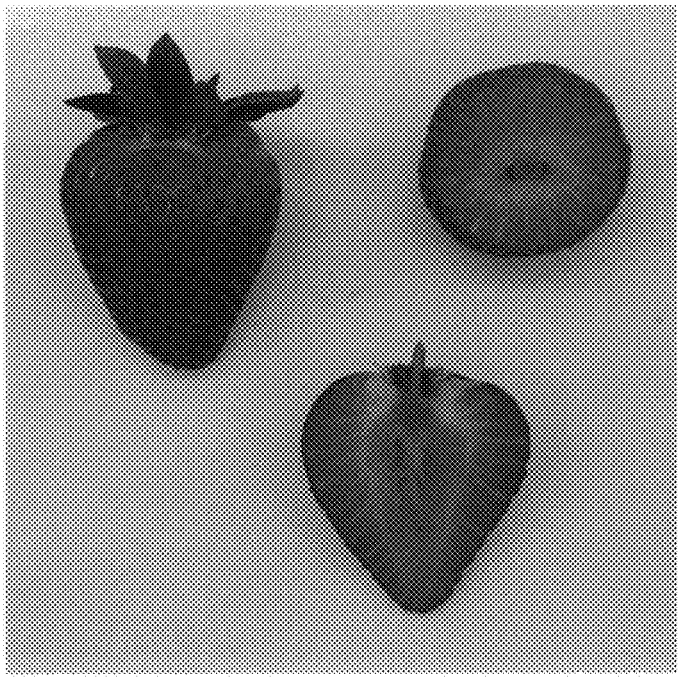

The photograph in FIG. 2 provides a close-up of the fruit of 'JFK44'.

Figure 3:
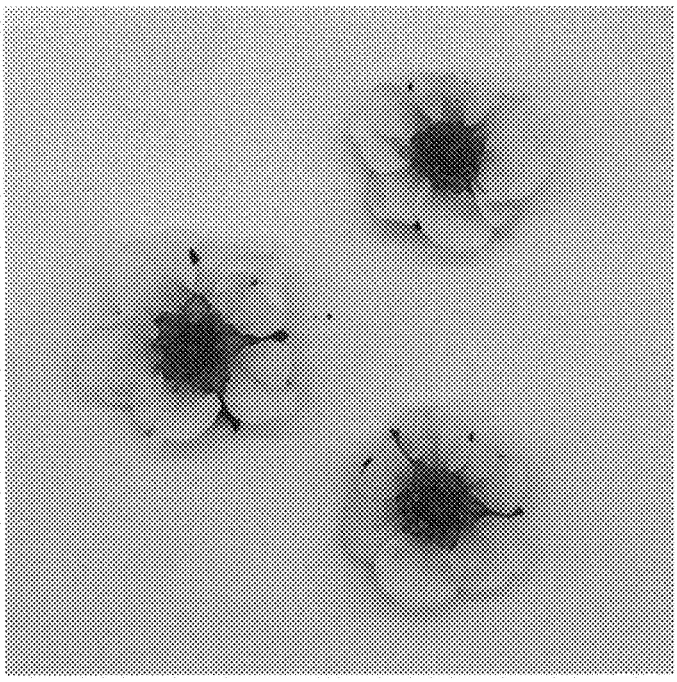

FIG. 3 provides a close-up view of the flowers of 'JFK44'.

The colors in the photographs are as close as possible with digital photography techniques available, the color values cited in the detailed botanical description accurately describe the colors of the *Fragaria*.

DETAILED BOTANICAL DESCRIPTION

The following is a detailed description of fruiting plants of 'JFK44' as grown in trays under polythene tunnels in substrate in Faversham, Kent, United Kingdom. The description were taken 3 months after planting in January from tips taken in June the year before and grown in a container until December and overwintered at −2° C. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—April in Faversham, Kent, United Kingdom.

*Plant type*.—Herbaceous fruit producing perennial.

*Plant habit*.—Semi-upright, vigorous with a dense canopy.

*Height and spread*.—Large: reaches an average of 40.9 cm in height and 6.3 cm in width (at the base).

*Cold hardiness*.—Not tested in areas where temperatures as low as 32° F. occur.

*Diseases*.—A slight susceptibility to *Podosphaera leucotricha* (powdery mildew) has been observed.

*Root description*.—Fibrous, white in color.

*Root development*.—An average of 2 weeks to initiate roots and 5 weeks to produce a young rooted plant.

*Propagation*.—Rooting of stolons and tissue culture.

*Growth rate*.—Vigorous.

*Stem description*.—Acaulescent.

*Stolon description*.—Produced throughout the cropping season; surface pubescence is sparse and anthocyanin coloration is medium.

Foliage description:

*Leaf division*.—Trifoliate.

*Leaf arrangement*.—Basal.

*Leaf attachment*.—Petiolate.

*Leaflet shape*.—Ovate, longer than wide.

*Mid-tier leaflet size*.—Average of 11.5 cm in length and 10.5 cm in width.

*Leaflet margins*.—Serrate to crenate, an average of 21.4 serrations per leaf.

*Leaflet base*.—Acute.

*Leaflet apex*.—Round.

*Leaflet glossiness*.—Upper surface medium, lower surface absent.

*Leaflet aspect*.—Most leaflets are concave and overlapping.

*Leaflet interveinal blistering*.—Moderate.

*Leaflet venation*.—Pinnate, coloration matches leaflet color.

*Leaflet surface*.—Upper surface mostly glabrous, lower surface slightly pubescent, particularly along the vein, with moderate blistering depending on leaf age.

*Leaflet color*.—Upper surface 137A, lower surface 138B, no variegation present on either surface.

*Petiole*.—Round in shape, average of 17.7 cm in length and 3.6 mm in width, 144C in color, moderate to pubescent surface with hairs horizontal in their attitude.

*Petiolules*.—Round in shape, average of 1.5 cm in length and 3.4 cm in width, moderately pubescent surface, 144C in color.

*Stipule*.—Average of 2.5 cm in length, moderate anthocyanin 67C in color.

Flower description:

*Inflorescence*.—Truss.

*Inflorescence size*.—Long in length, average of 36.9 cm and 5.9 mm in width. Average of 22.1 cm in long before branching.

*Time of flowering* (50% *of plants at first flower*).—Early, April.

*Flower position relative to foliage*.—Mostly level with foliage.

*Flower size*.—Average corolla diameter of 3.8 cm.

*Flower number per truss*.—Average of 6.

*Calyx*.—Average of 2.9 cm in diameter, smaller than the corolla, mostly upwards, re-curved relative to fruit.

*Sepals*.—Average number of 11.2 per flower, oblong to oblanceolate in shape, 138B in color on upper surface, N138B in color on lower surface, obtuse base, acute apex, entire margin, almost no pubescence on upper surface and light pubescence on lower surface.

*Sepal position*.—Mixed arrangement relative to the fruit, most horizontal to recurving with fruit shoulder, however not touching the fruit.

*Petals*.—Average of 5.4 in number with an average of 1.23 cm in length and 1.42 cm in width: a length to width ratio averaging 0.86, rounded in shape, obtuse base and apex, each arranged touching or overlapping, entire margins, upper and lower surface glabrous and N155B in color.

*Peduncle*.—Low density of pubescence on surface, upward attitude of hairs, strong in strength.

*Pedicel*.—Low density of pubescence on surface, upward attitude of hairs, strong in strength.

Reproductive organs:

*Gynoecium*.—Average of 9.4 mm in width, steeply dome shaped, multiple simple pistils present with capitate shaped stigma.

*Androecium*.—Stamens; average of 30, average of 4 mm in length, shape is a cone-like tube and wider at the base, anther; 17B in color, oval in shape, average of 2.5 mm in length, pollen; moderate in quantity and 20B in color.

Fruit description:

*Shape*.—Predominantly conical, shape is similar for primary, secondary and tertiary fruit.

*Season of harvest*.—Early-June through Mid-July in Faversham, Kent, United Kingdom.

*Time of ripening* (50% *of plants with first ripe fruit*).—Early.

*Type of bearing*.—June Bearing.

*Size*.—Large; an average of 4.9 cm in length and 4.2 cm in width.

*Surface*.—Smooth and highly glossy.

*Calyx position*.—Mostly level with fruit and mostly re-curved.

*Attitude of calyx segments*.—Mostly upwards recurved, very few touching the fruit shoulder with strong adherence to the fruit.

*Diameter of calyx relative to fruit diameter*.—Size is similar to fruit diameter in majority of fruit.

*Glossiness*.—Even and high.

*External color* (*skin*).—N45B, color is retained throughout the cropping season.

*Internal color* (*flesh*).—Near skin; 44A, near center; 31C.

*Evenness of color of skin*.—Very even.

*Evenness of color of flesh*.—Paler near center.

*Acidity*.—Low, average 0.49% total titratable acid over three seasons in trials.

*Sweetness*.—Medium.

*Soluble solids*.—Average of 8.0° over three seasons in trials.

*Firmness*.—Skin is moderately firm (resistant to bruising), flesh is moderately firm.

*Juiciness*.—High.

*Aroma*.—Slight.

*Weight*.—Average of 33.9 g per berry and 790 g per plant from early-June through Mid-July over three seasons in trials.

*Number of fruit per plant*.—Average of 25 from early-June through Mid-July to mid-July over three seasons in trials.

*Hollow center*.—Medium sized cavity observed on some fruit, more so on primaries.

*Shelf life*.—Good.

*Achene color*.—Majority 1B.

*Achene position*.—Mostly level with surface.

*Achene number*.—An average of 261 per berry.

*Band without achenes*.—Absent or very narrow.

It is claimed:

1. A new and distinct cultivar of *Fragaria* plant named 'JFK44' as herein illustrated and described.

* * * * *